United States Patent
Dicke et al.

(10) Patent No.: US 6,644,121 B2
(45) Date of Patent: Nov. 11, 2003

(54) ON-LINE MEASUREMENT SYSTEM FOR PRODUCT FORMED IN A CONTINUOUS MANNER AND METHOD THEREFOR

(75) Inventors: Timothy T. Dicke, Beavercreek, OH (US); Ronald Adkins, Hamilton, OH (US)

(73) Assignee: Beta LaserMike, Inc., Dayton, OH (US)

( * ) Notice: Subject to any disclaimer, the term of this patent is extended or adjusted under 35 U.S.C. 154(b) by 65 days.

(21) Appl. No.: 10/002,687

(22) Filed: Oct. 24, 2001

(65) Prior Publication Data

US 2003/0074969 A1 Apr. 24, 2003

(51) Int. Cl.$^7$ ............................................. G01N 29/00
(52) U.S. Cl. ............................. 73/602; 73/579; 73/657
(58) Field of Search ........................ 73/602, 579, 597, 73/598, 599, 600, 609, 610, 611, 625, 628, 641, 643, 644, 657, 646, 1.15, 770

(56) References Cited

U.S. PATENT DOCUMENTS

| | | | | |
|---|---|---|---|---|
| 3,690,154 A | * | 9/1972 | Wells et al. | 73/615 |
| 4,291,577 A | * | 9/1981 | Baum et al. | 73/597 |
| 4,976,150 A | * | 12/1990 | Deka | 73/644 |
| 5,042,303 A | * | 8/1991 | Geluk et al. | 73/602 |
| 5,237,874 A | * | 8/1993 | Latimer et al. | 73/621 |
| 5,398,538 A | * | 3/1995 | Williams et al. | 73/1.37 |
| 5,457,362 A | * | 10/1995 | Bitzer et al. | 318/116 |
| 5,578,764 A | * | 11/1996 | Yokoi et al. | 73/861.356 |
| 5,608,165 A | * | 3/1997 | Mozurkewich, Jr. | 73/599 |
| 5,676,147 A | * | 10/1997 | Petrofsky et al. | 600/447 |
| 5,804,727 A | * | 9/1998 | Lu et al. | 73/597 |
| 6,502,463 B1 | * | 1/2003 | Clark et al. | 73/643 |

OTHER PUBLICATIONS

Fujimoto et al. (2002/007378), Angular velocity sensor.*
Innovation News, p. 1, Mar. 1999.
System 6006 Ultrasonic Gauging System Operator's Manual, pp. 1, 2–4, 2–5, 3–14, 3–15, 3–16, 3–17, 3–18, 3–19, 3–20, 3–21, Jan. 2001.
Electronic Unit UMAC 8K, pp. 1, 6, 9, 10, 12, 13, 20, 21, May 1996.

* cited by examiner

Primary Examiner—Hezron Williams
Assistant Examiner—Jacques Saint-Surin
(74) Attorney, Agent, or Firm—R. William Graham

(57) ABSTRACT

An improvement in an on-line measurement system for product formed in a continuous manner includes a device for receiving a first waveform signal indicative of a presence of a first characteristic of the product and a second waveform signal indicative of a presence of a second characteristic of the product. A computer based device having phase shifting software is provided for shifting phase of each of the first waveform signal and the second waveform signal a predetermined amount to produce a respective first transformed waveform signal and a second transformed waveform signal. Further, software is provided in the computer based device for combining the first waveform signal and the first transformed waveform signal in manner to produce a first rectified waveform having an increasingly defined peak and for combining the second waveform signal and the second transformed waveform signal in manner to produce a second rectified waveform having an increasingly defined peak, wherein the peaks are useful in the in-line measurement system for defining a third characteristic of the product. A method employing the invention is also provided.

20 Claims, 7 Drawing Sheets

ON-LINE MEASUREMENT SYSTEM FOR PRODUCT FORMED IN A CONTINUOUS MANNER AND METHOD THEREFOR

BACKGROUND OF THE INVENTION

1. Field of the Invention

The present invention relates to on-line measurement systems, an in particular to automating the setup of such systems for the measurement of extruded products using an ultrasonic gauge.

2. Related Art

Ultrasonics provides an ideal mechanism to monitor extruded products where information about internal dimensions and possible defects is desired. These extruded products can be made of one or more layers of different materials. These different layers of material may serve different purposes in the product, and they may have a wide range in price. The manufacturer wishes to control the extrusion process to always exceed the minimum performance requirements for the product, while also using the minimum amount of material. If they have real time information about the product, the extrusion process can be controlled to produce the desired result.

An ultrasonic signal, or impulse is transmitted to the product by way of a transducer. This impulse will be injected into the extruded material by way of way of a coupling medium, which is often water. The acoustic properties of the materials differ from one another, and from the medium through with they are moving, creating interface regions that can be detected. At such an interface, some of the ultrasonic signal will be reflected back toward its point of origin. This reflected signal can be detected by the same transducer that created the original signal, or by another. The round trip time between when the impulse was created and when the reflected signal is detected is multiplied by the speed of sound in the material to get the thickness of the layer. By measuring the thickness of every layer, the total thickness of the product at that point can be calculated. When this measurement is repeated at several points around the product, a more detailed understanding of the extrusion process can be created. Additional measurements, such as the concentricity of the layers can be determined, adding additional value to the measurement and control system.

These measurement and control systems have existed for some time and have been progressing from Analog Measurement Systems to Digital Measurement System. The older analog systems require a lot of experience to set up and run accurately. Each time the product being made is changed, a new setup must be made. This setup involves the operator looking at the raw signals, and using their experience to adjust the system to get a good measurement. This process relies heavily on the experience of the operator, and requires that more experienced personnel are employed to manufacture the products. This is also time consuming, and while the system is being adjusted, the extruder is making product that will have to be scrapped because it is of unknown quality. This can be very expensive, depending on the type of product being manufactured.

The newer digital measurement systems have introduced some automation to the set up of these extrusion control systems. They often will be able to set up most of the required parameters automatically, when used with thick, single layer extrusions. These types of products generate a simple electrical signal, which is relatively easy for the computer to interpret. They still have difficulty with multiple layered products, especially if they include thin layers, which require the operator to manually adjust some of the parameters. While better than the older analog systems, they still are not user friendly, and rely too heavily on the experience of the operator to get an accurate reading.

SUMMARY OF THE INVENTION

It is an object of the invention to improve on-line measurement systems for products formed in a continuous manner.

It is another object to improve on-line wall thickness and concentricity measurement for product formed in a continuous manner.

It is another object to simplify operation of on-line measurement of product formed in a continuous manner.

It is yet another object to increase the accuracy of on-line measurement for product formed in a continuous manner.

It is yet another object to provide a more robust on-line measurement system for product formed in a continuous manner.

Still another object is to reduce waste of product by improving on-line measurement system for product formed in a continuous manner Accordingly, the invention is directed to an improvement in an on-line measurement system for product formed in a continuous manner. The improvement includes a device for receiving a first waveform signal indicative of a presence of a first characteristic of the product and a second waveform signal indicative of a presence of a second characteristic of the product. A computer based device having phase shifting software is provided for shifting phase of each of the first waveform signal and the second waveform signal a predetermined amount to produce a respective first transformed waveform signal and a second transformed waveform signal. Further, software is provided in the computer based device for combining the first waveform signal and the first transformed waveform signal in manner to produce a first rectified waveform having an increasingly defined peak and for combining the second waveform signal and the second transformed waveform signal in manner to produce a second rectified waveform having an increasingly defined peak, wherein the peaks are useful in the in-line measurement system for defining a third characteristic of the product. A method employing the invention is also provided.

The first characteristic is an indicia of a first wall side of the product. The second characteristic is an indicia of a second wall side of the product and the third characteristic is an indicia of a wall thickness between the first wall side and the second wall side of the product.

Other objects and advantages will be readily apparent to those skilled in the art upon viewing the drawings and reading the detailed description hereafter.

DETAILED DESCRIPTION

Figure 1:
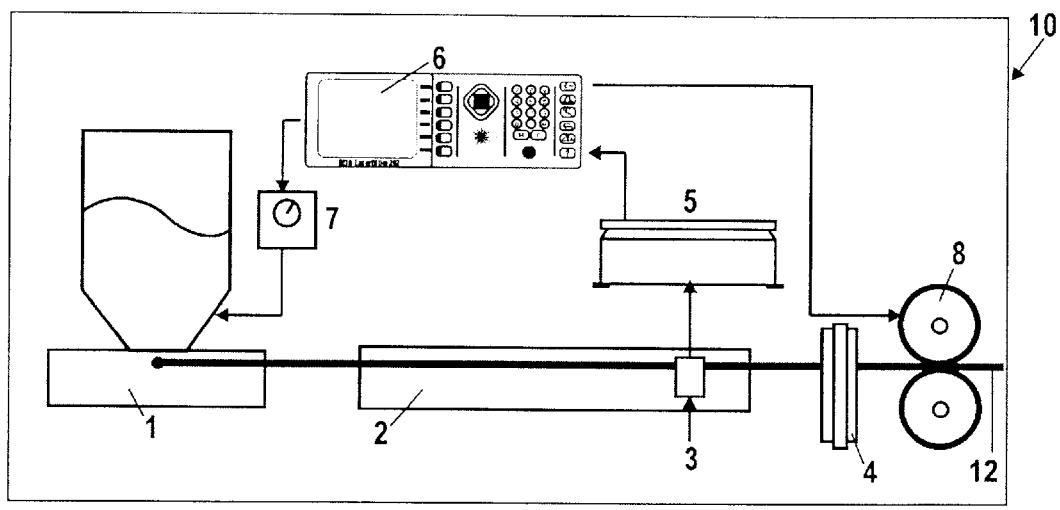
FIG. 1 is a schematic of view of an improved on-line measurement system of the present invention in a system for forming continuous product.

Referring now to the drawings, the present invention is generally directed to an improved computer based on-line measurement system 5 which is operably connected to a continuous forming system 10 for forming product 12 in a continuous manner, such as extrusion or pultrusion, for example. However, the system 10 and method for forming product 12 is not intended to be limiting of the application of the invention.

The system 10 as shown in the embodiment herein includes an extruder 1 which is operably connected to an extruder speed control 7 which is in turn operably connected to a controller 6. The extruder 1 is operably associated with a cooling trough 2 which receives the extruded product 12. Disposed downline within the trough 2 is an ultrasonic gauge 3 which is shown in greater detail in FIG. 2. The gauge 3 is operably connected to the improved on-line measurement system 5 which in turn is operably connected to the controller 6. Further, system 10 includes a laser diameter gauge device 4 through which the product 12 moves. The product 12 is taken up through a conventional take-up device 8 as is known in the industry. The controller 6 is also operably connected to the take up device 8 to control take up speed.

Figure 2:
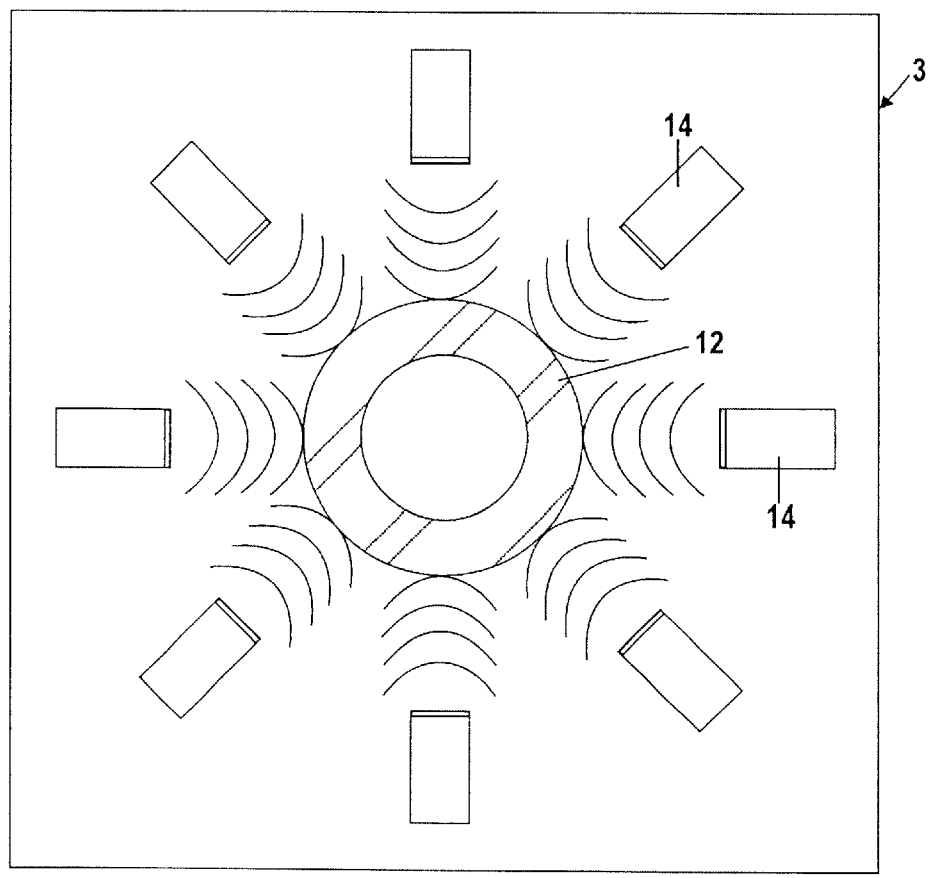
FIG. 2 is a cross sectional schematic of an ultrasonic head gauge for use with the present invention.
Figure 3:
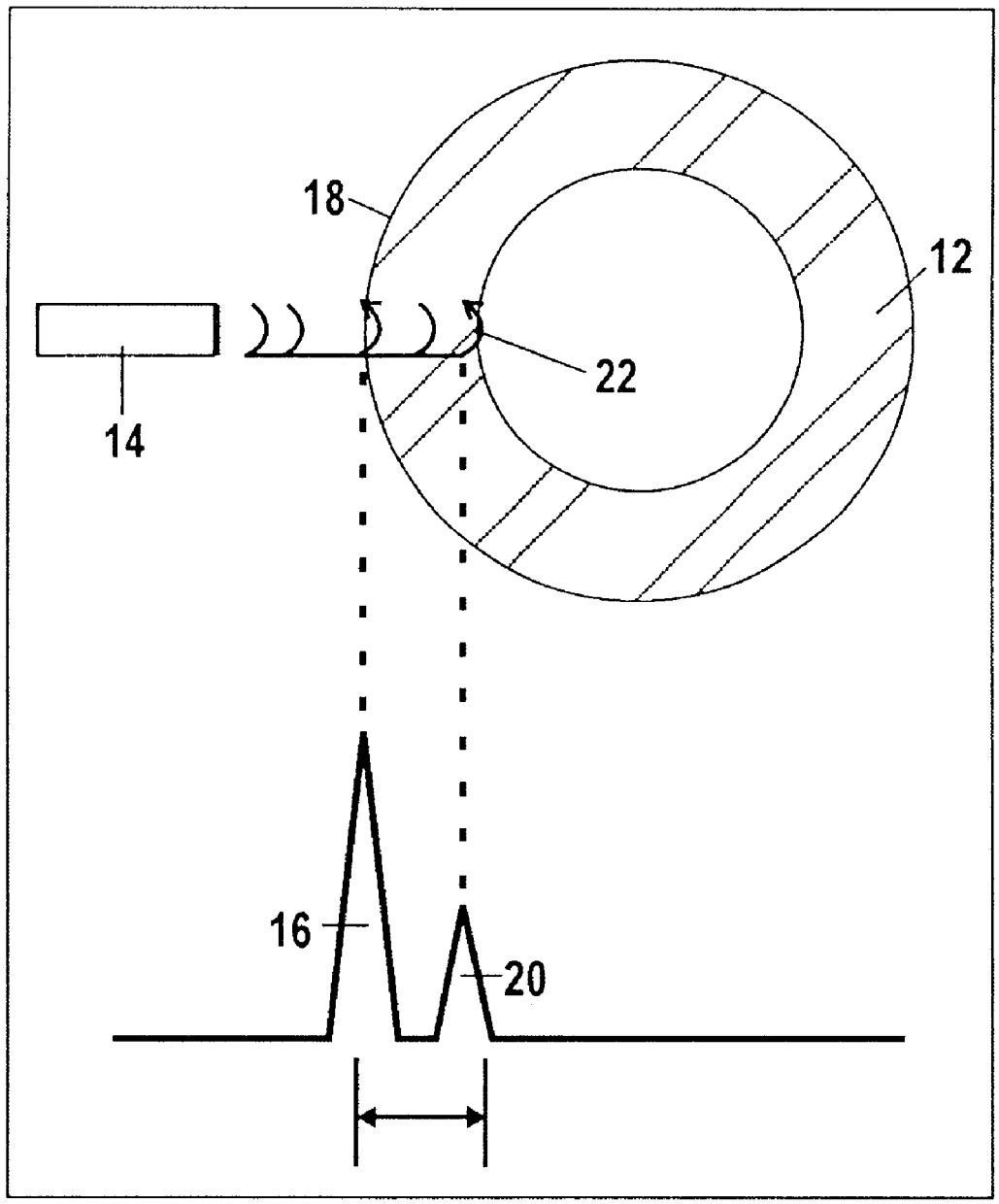
FIG. 3 is a cross-sectional schematic view of a principle for measuring used in the present invention.
Figure 4:
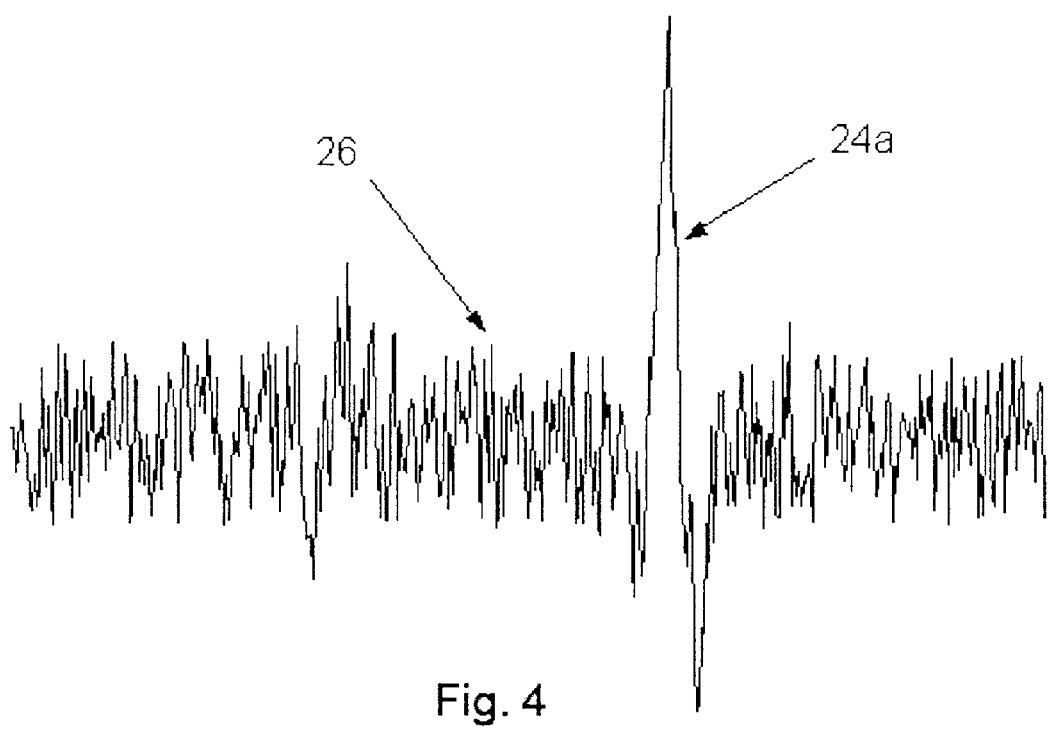
FIG. 4 is schematic of a waveform.
Figure 5:
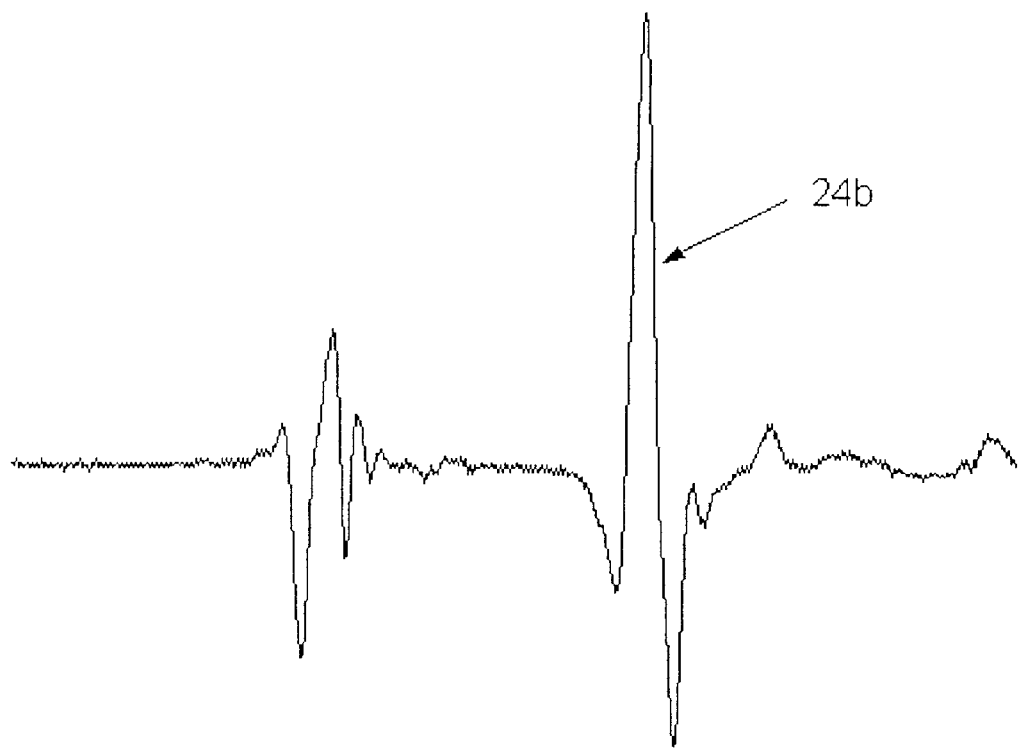
FIG. 5 is schematic of a filtered waveform.
Figure 6:
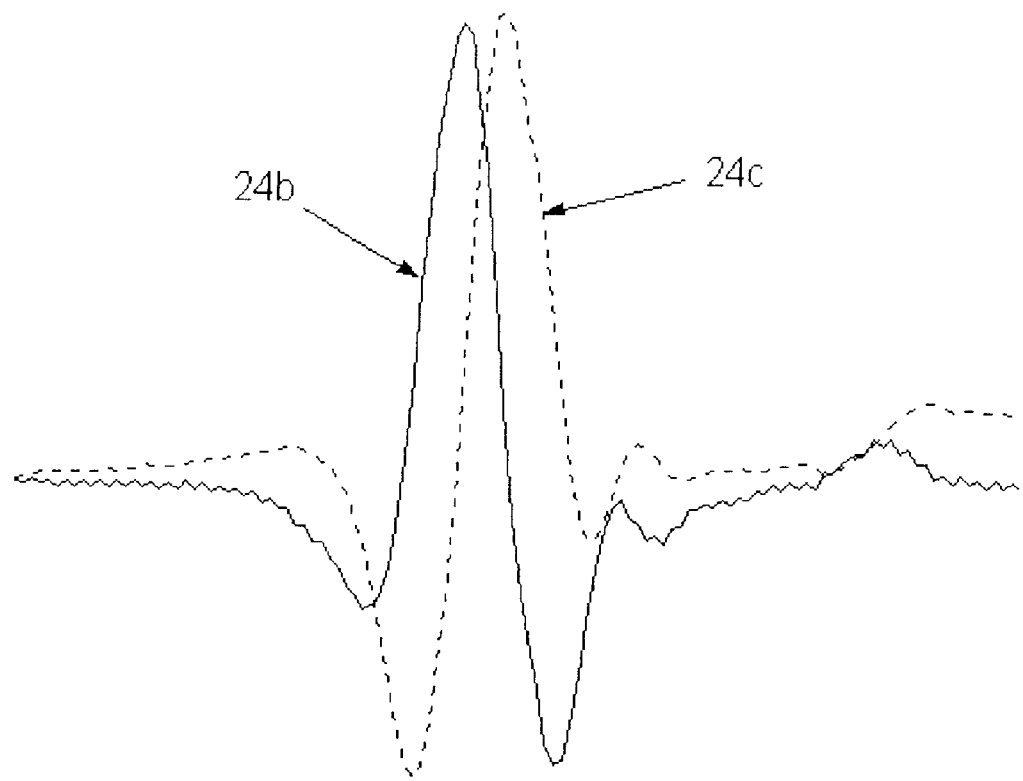
FIG. 6 is schematic of a transformed waveform.
Figure 7:
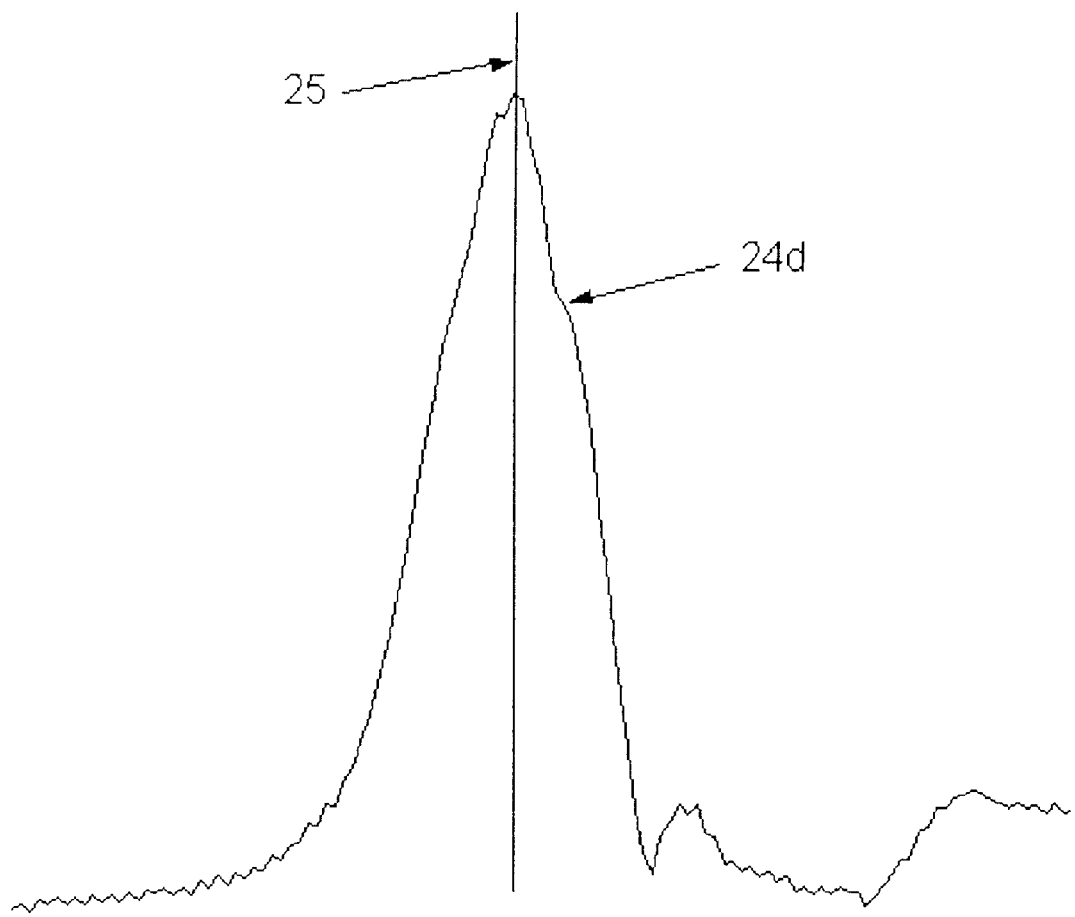
FIG. 7 is schematic of a rectified waveform.

FIG. 2 shows the gauge 3 which includes a plurality of transducers 14 radially disposed around the product 12. The transducers 14 are capable of producing and measuring ultrasonic signals which are bounced off the product 12, as seen in FIG. 3. The returned waveform signal 16 (exemplary only) is indicative of the presence of a wall side portion 18 whereas the waveform signal 20 (exemplary only) is indicative of the presence of a wall side portion 20. While not shown, the transducers 14 are capable of measuring multiple or different layers of a product.

The transducers 14 pick up and transmit a first waveform signal 24 to the improved on-line measurement system 5. The signal 24 typically includes a significant amount of noise 26 which is not desirable for purposes of gaining useful information from the waveform signal 24a.

Figure 8:
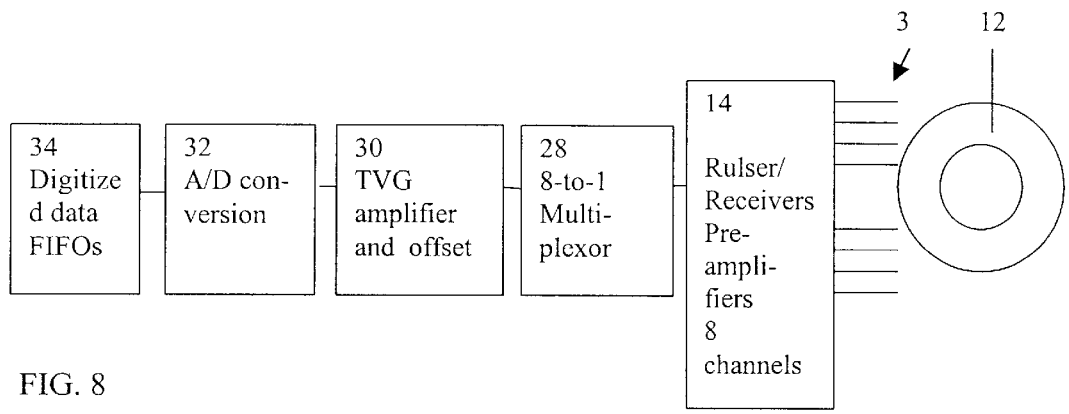
FIG. 8 is a block diagram of preprocessing employed by the invention.

FIG. 8 shows a hardware block diagram wherein the gauge 3 and transducers 14 are operably connected in series to a multiplexor 28, time varied gain amplifier and offset 30, analog/digital converter 32 and memory block 34 for writing digitized data in a first in first out (FIFO) manner. These elements are employed to maximize and/or normalize the waveform signals which are received from the transducers 14.

Figure 9:
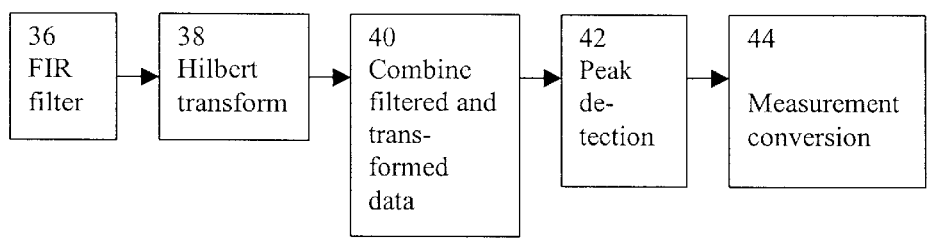
FIG. 9 is a schematic of a block diagram of the process employed by the invention.

Referring now to FIG. 9, The improved on-line measurement system 5 receives the waveform signal 24a and performs a noise filtering process 36 which produces a filtered waveform signal 24b. The noise filtering process can be of a type such as a finite impulse response. The waveform signal 24a, for example, can be indicative of a presence of a first characteristic (outer wall presence) of the product 12, and as a function of time can be indicative of a presence of a second characteristic (an inner wall) of the product.

The filtered waveform signal 24b is processed by phase shifting software 38 for example, a Hilbert transform function, which phase shifts the filtered waveform 24b by 90° to produce a transformed waveform 24c. Rectifying software 40 is provided for combining the filtered waveform signal 24b and the transformed shifted waveform signal 24c in manner to produce a rectified waveform signal 24d having an increasingly defined peak 25.

The defined peak 25 is located by software 42 and analyzed by operating software 44 bothon the on-line measurement system 5 in relation to predetermined data configuration characteristic of the product 12, such as the number of layer walls thereof. To further the process of the on-line measurement system 5, the peaks 25 and predetermined data configuration (such as number of layered walls for the product 12) are analyzed to determine the peaks are in fact indicative of the presence of a wall, layer or portion thereof. This determination is thus used by the controller 6 as part of the automated setup provided by the invention.

The above described embodiments is set forth by way of example and is not for the purpose of limiting the present invention. It will be readily apparent to those skilled in the art that obvious modifications, derivations and variations can be made to the embodiments without departing from the scope of the invention. Accordingly, the claims appended hereto should be read in their full scope including any such modifications, derivations and variations.

What is claimed is:

1. An improvement in an on-line measurement system for product formed in a continuous manner, which includes:

means for receiving a first waveform signal indicative of a presence of an indicia of a first wall side of the product and a second waveform signal indicative of a presence of an indicia of a second wall side of the product;

means for shifting phase of each said first waveform signal and said second waveform signal by a predetermined amount to produce a respective first transformed waveform signal and a second transformed waveform signal; and means for combining said first waveform signal and said first transformed waveform signal in manner to produce a first rectified waveform having an increasingly defined peak and for combining said second waveform signal and said second transformed waveform signal in manner to produce a second rectified waveform having an increasingly defined peak, wherein said peaks are useful the on-line measurement system for defining an indicia of a wall thickness between said first wall side and said second wall side of the product.

2. The improvement in an on-line measurement system of claim 1, which further includes:

means for receiving a third waveform signal indicative of a presence of an indicia of a third wall side portion of the product and fourth waveform signal indicative of a presence of an indicia of a fourth wall side portion of the product;

means for shifting phase of each said third waveform signal and said fourth waveform signal a predetermined amount to produce a respective third transformed waveform signal and a fourth transformed waveform signal; and means for combining said third waveform signal and said third transformed waveform signal in manner to produce a third rectified waveform having an increasingly defined peak and for combining said fourth waveform signal and said fourth transformed waveform signal in manner to produce a fourth rectified waveform having an increasingly defined peak, wherein said peaks are useful in the on-line measurement system for defining an indicia of a wall thickness between said fourth wall side portion and said fifth wall side portion of the product.

3. The improvement in an on-line measurement system of claim 2 wherein the product is tubular and said third indicia and said sixth indicia are used by the system for determining concentricity.

4. The improvement in an on-line measurement system of claim 2, wherein said phase shift is performed at 90°.

5. The improvement in an on-line measurement system of claim 2, which further includes means for filtering noise from said first waveform signal, said second waveform signal said third waveform signal, and said fourth waveform signal.

6. The improvement in an on-line measurement system of claim 1, wherein said phase shift is performed at 90°.

7. The improvement in an on-line measurement system of claim 1, which further includes means for filtering noise from said first waveform signal and said second waveform signal.

8. The improvement in an on-line measurement system of claim 1, which further includes means for analyzing predetermined data configuration characteristic of the product and said peak to make a determination whether said peak is indicative of one of said characteristics.

9. The improvement in an on-line measurement system of claim 8, which further includes means utilizing said determination for providing an automated setup for said on-line measurement system.

10. The improvement in an on-line measurement system of claim 8, wherein said characteristics includes one of presence of a wall, wall layer and portion thereof.

11. A method for improving on-line measurement of product formed in a continuous manner, which includes the steps of:
receiving a first waveform signal indicative of a presence of an indicia of a first wall side of the product and a second waveform signal indicative of an indicia of a second wall side of the product;
phase shifting each said first waveform signal and said second waveform signal by a predetermined amount to produce a respective first transformed waveform signal and a second transformed waveform signal;
combining said first waveform signal and said first transformed waveform signal in manner to produce a first rectified waveform having an increasingly defined peak; and combining said second waveform signal and said second transformed waveform signal in manner to produce a second rectified waveform having an increasingly defined peak, and using said peaks in the on-line measurement system for defining an indicia of a wall thickness between said first wall side and said second wall side of the product.

12. The method of claim 11, which further includes:
receiving a third waveform signal indicative of a presence of an indicia of a third wall side portion of the product and fourth waveform signal indicative of a presence of an indicia of a fourth wall side portion of the product;
phase shifting each said third waveform signal and said fourth waveform signal by a predetermined amount to produce a respective third transformed waveform signal and a fourth transformed waveform signal;
combining said third waveform signal and said third transformed waveform signal in manner to produce a third rectified waveform having an increasingly defined peak;
combining said fourth waveform signal and said fourth transformed waveform signal in manner to produce a fourth rectified waveform having an increasingly defined peak; and
using said peaks in the on-line measurement system for defining an indicia of a wall thickness between said fourth wall side portion and said fifth wall side portion of the product.

13. The method of claim 12, wherein the product is tubular and said third indicia and said sixth indicia are used by the system for determining concentricity.

14. The method of claim 12, wherein said phase shifting is performed at 90°.

15. The method of claim 12, which further includes the step of filtering noise from said first waveform signal, said second waveform signal, said third waveform signal, and said fourth waveform signal prior to said step of phase shifting.

16. The method of claim 11, wherein said phase shifting is performed at 90°.

17. The method of claim 11, which further includes the step of filtering noise from said first waveform signal and said second waveform signal prior to said step of phase shifting.

18. The method of claim 11, which further includes the step of analyzing predetermined data configuration characteristic of the product and said peak to make a determination whether said peak is indicative of one of said characteristics.

19. The method of claim 18, which further includes the step of using said determination to provide an automated setup for said on-line measurement system.

20. The method of claim 18, wherein said characteristics includes one of presence of a wall, wall layer and portion thereof.

* * * * *